(12) United States Patent
Hawkins (10) Patent No.: US 6,793,678 B2
(45) Date of Patent: Sep. 21, 2004

(54) PROSTHETIC INTERVERTEBRAL MOTION DISC HAVING DAMPENING

(75) Inventor: John Riley Hawkins, Cumberland, RI (US)

(73) Assignee: DePuy Acromed, Inc., Raynham, MA (US)

( * ) Notice: Subject to any disclaimer, the term of this patent is extended or adjusted under 35 U.S.C. 154(b) by 0 days.

(21) Appl. No.: 10/400,969

(22) Filed: Mar. 27, 2003

(65) Prior Publication Data

US 2004/0002762 A1 Jan. 1, 2004

(51) Int. Cl.[7] ............................. A61F 2/44; A61F 2/30; A61F 2/28; A61B 17/56; A61B 17/58
(52) U.S. Cl. ...................... 623/17.15; 623/23.5; 606/61
(58) Field of Search ............... 623/11.11, 16.11, 623/17.11, 17.15, 17.16, 23.5; 606/60, 61

(56) References Cited

U.S. PATENT DOCUMENTS

| | | | |
|---|---|---|---|
| 3,867,728 A | * | 2/1975 | Stubstad et al. ......... 623/17.16 |
| 5,171,281 A | * | 12/1992 | Parsons et al. .......... 623/17.15 |
| 5,314,477 A | | 5/1994 | Marnay |
| 5,401,269 A | | 3/1995 | Buttner-Janz et al. |
| 5,507,816 A | | 4/1996 | Bullivant |
| 5,545,229 A | * | 8/1996 | Parsons et al. .......... 623/17.15 |
| 5,556,431 A | * | 9/1996 | Buttner-Janz ............ 623/17.15 |
| 5,676,701 A | | 10/1997 | Yuan et al. |
| 5,782,832 A | * | 7/1998 | Larsen et al. ................ 606/61 |
| 6,063,121 A | * | 5/2000 | Xavier et al. ............ 623/17.15 |
| 6,368,350 B1 | | 4/2002 | Erickson et al. |
| 6,517,580 B1 | * | 2/2003 | Ramadan et al. ......... 623/17.15 |
| 6,579,320 B1 | * | 6/2003 | Gauchet et al. .......... 623/17.15 |
| 2003/0135277 A1 | * | 7/2003 | Bryan et al. ............. 623/17.12 |

FOREIGN PATENT DOCUMENTS

| | | | | |
|---|---|---|---|---|
| FR | 2 730 159 A1 | | 2/1995 | |
| WO | WO 9822050 | * | 5/1998 | ............. A61F/2/44 |
| WO | WO 01/68003 | * | 3/2001 | ............. A61F/2/44 |

OTHER PUBLICATIONS

U.S. patent application Ser. No. 60/391,845, DePuy AcroMed, pending.

* cited by examiner

*Primary Examiner*—Eduardo C. Robert
*Assistant Examiner*—Anuradha Ramana (57) ABSTRACT

An articulating motion disc having a core member that expands laterally in response to an axial load to mimic the shock absorbing function of a natural intervertebral disc.

18 Claims, 6 Drawing Sheets

PROSTHETIC INTERVERTEBRAL MOTION DISC HAVING DAMPENING

BACKGROUND OF THE INVENTION

In a normal spine, a healthy intervertebral disc can compress about 1 mm when subjected to an axial load of 750 pounds force (3.4 kN). This compression provides the spine with an effective shock absorber against high loads.

The leading cause of lower back pain arises from rupture or degeneration of lumbar intervertebral discs. Pain in the lower extremities is caused by the compression of spinal nerve roots by a bulging disc, while lower back pain is caused by collapse of the disc and by the adverse effects of articulation weight through a damaged, unstable vertebral joint. One proposed method of managing these problems is to remove the problematic disc and replace it with a prosthetic disc that allows for the natural motion between the adjacent vertebrae ("a motion disc").

However, it appears that conventional articulating motion discs do not provide the shock absorbing function of a natural intervertebral disc.

U.S. Pat. No. 6,368,350 ("Erickson") discloses a three-piece articulating motion disc providing two articulation surfaces. The disc comprises a first piece having a curved surface, a second piece having a flat surface, and an intermediate piece (or "core") having a corresponding curved articulation surface and a corresponding flat articulation surface. Erickson discloses essentially unitary core components that must be made from "non-compressible" materials. See Erickson at col. 5, lines 49–50. Accordingly, Erickson does not teach a device having the shock absorbing function of a natural intervertebral disc.

U.S. Pat. No. 5,676,701 ("Yuan") discloses, in one embodiment, a motion disc having a single articulation surface. This device includes a first component whose inner surface comprises a concave inner portion having a 360° circumference and a convex peripheral portion, and an opposing second component whose inner surface comprises a conforming convex inner portion and a convex peripheral portion. The convex/concave contours of the opposing inner portions form a ball-and-socket design that allows unrestricted pivotal motion of the device, while the opposing convex peripheral contours allow flexion/extension bending motion in the range of about 20–30°. In another embodiment, Yuan discloses a device having two articulation interfaces, wherein one of the above-mentioned components is made in two pieces having opposing flat surfaces that form a translation interface to further provide the prosthetic with a certain amount of translation. See FIG. 9 of Yuan. Yuan discloses essentially unitary components made from essentially incompressible materials, such as ceramics, metals and high density polyethylene. See Yuan at col.6, lines 8–14. Accordingly, Yuan does not teach a device having the shock absorbing function of a natural intervertebral disc.

U.S. Pat. No. 5,507,816 ("Bullivant") discloses a three-piece articulating motion disc providing two articulation interfaces and comprises an upper piece having a flat lower surface, a middle spacer having a flat upper surface and a convex lower surface, and a lower piece having a concave upper surface. The articulating convex and concave surfaces form an articulating interface that allows pivotal motion, while the flat surfaces form a translation interface that allows translational motion. Bullivant further teaches that the natural tension of the vertebrae ensures that the vertebrae are biased together to trap the spacer in place, and that the 90° extension of the convex and concave surfaces virtually eliminates any chance of the spacer escaping from between the plates under normal pivotal movement of the vertebrae. Bullivant discloses an essentially unitary core component made from polyethylene. See Bullivant at col. 4, line 28. Accordingly, Bullivant does not teach a device having the shock absorbing function of a natural intervertebral disc.

U.S. Pat. No. 5,401,269 ("Buttner-Janz") discloses an articulating motion disc having two articulation interfaces and comprises three components: an inferior endplate, a superior endplate, and a core. Both the inferior and superior endplates are metal and have raised bosses with concave spherical surfaces in the center. The core is plastic and has convex surfaces on both the top and bottom which are surrounded by raised rims. Buttner-Janz discloses an essentially unitary core component made from high density polyethylene. See Buttner-Janz at col. 3, line 4. Accordingly, Buttner-Janz does not teach a device having the shock absorbing function of a natural intervertebral disc.

U.S. Pat. No. 5,314,477 ("Marnay") discloses an articulating motion disc having a single articulation interface and comprises three components: an inferior endplate, a superior endplate, and an insert. The inferior endplate functions as a baseplate and has a sidewall forming an open ended channel for reception of the insert. The inner surface of the inferior endplate provides only stationary support for the insert and does not have a motion surface. Since the insert is designed to be locked securely into place within the inferior endplate, the inferior surface of the insert is not a motion surface. The superior surface of the insert includes articulation surface for articulation with the superior endplate. The superior endplate has an inferior articulation surface that articulates with the superior motion surface of the insert, and a superior surface designed for attachment to a vertebral endplate.

French Published Patent Application No. 2,730,159 ("Germain") discloses an articulating motion disc in which the core member has one convex and concave surface. Germain further teaches that the radius of the upper curved surface (3a) of the core member is less than the radius of the lower curved surface (3b) of the core member.

In summary, in all of the conventional motion discs having a core articulation component, the core is unitary and made of a material having a significantly high stiffness. Accordingly, these conventional devices may not fully mimic the shock absorbing function of the natural intervertebral disc.

Therefore, there is a need for a motion device having a core component having two articulation interfaces, wherein the core component has a shock absorbing function mimicking the shock absorbing function of the natural intervertebral disc.

SUMMARY OF THE INVENTION

The present inventor has developed a motion disc having a core component that expands laterally under physiologic axial loads, thereby allowing the endplates of the disc to approach each other in order to mimic the shock-absorbing function of the natural disc.

Therefore, in accordance with the present invention, there is provided an intervertebral motion disc comprising:
 a) a first prosthetic vertebral endplate comprising:
  i) an outer surface adapted to mate with a first vertebral body,
  ii) an inner surface having a first articulation surface,
  iii) a body portion connecting the inner and outer surfaces, b) a second prosthetic vertebral endplate comprising:
  i) an outer surface adapted to mate with a second vertebral body,
  ii) an inner surface comprising a first articulation surface,
  iii) a body portion connecting the inner and outer surfaces, and
c) a laterally expandable core member comprising:
  a first articulation surface adapted for articulation with the first articulation surface of the first endplate,
  a second articulation surface adapted for articulation with the first articulation surface of the second endplate, wherein the core member is oriented therein to produce a first articulation interface between the first articulation surface of the first endplate and the first articulation surface of the core member, and a second articulation interface between the first articulation surface of the second endplate and the second articulation surface of the core member, and a height H between the outer surfaces of the prosthetic endplates, and wherein the laterally expandable core member expands laterally when the disc is subjected to axial load of about 750 pounds force (3.4 kN) to reduce the height of the device between 0.5 and 2.0 mm.

Also in accordance with the present invention, there is provided a core member for articulation between first and second prosthetic vertebral endplates, comprising:
  i) a first portion having a first articulation surface adapted for articulation with a first articulation surface of the first prosthetic vertebral endplate,
  ii) a second portion having a second articulation surface adapted for articulation with a first articulation surface of the second prosthetic vertebral endplate, and
  iii) means for transferring an axial load between the prosthetic endplates, wherein the core member is oriented therein to produce a first articulation interface between the first articulation surface of the first endplate and the first articulation surface of the core member, and a second articulation interface between the first articulation surface of the second endplate and the second articulation surface of the core member.

The disc of the present invention is superior to that of the above-mentioned conventional devices in that at least a portion of the core member expands laterally under physiologic axial loads, thereby allowing the endplates of the disc to approach each other in order to mimic the shock-absorbing function of the natural disc.

In preferred embodiments, the laterally expandable core member expands laterally when the disc is subjected to axial load of about 750 pounds force (3.4 kN) to reduce the height of the device between 0.5 and 2.0 mm.

DESCRIPTION OF THE FIGURES

FIG. 1b is an exploded cross sectional view of FIG. 1a.

DETAILED DESCRIPTION OF THE INVENTION

Figure 1A:
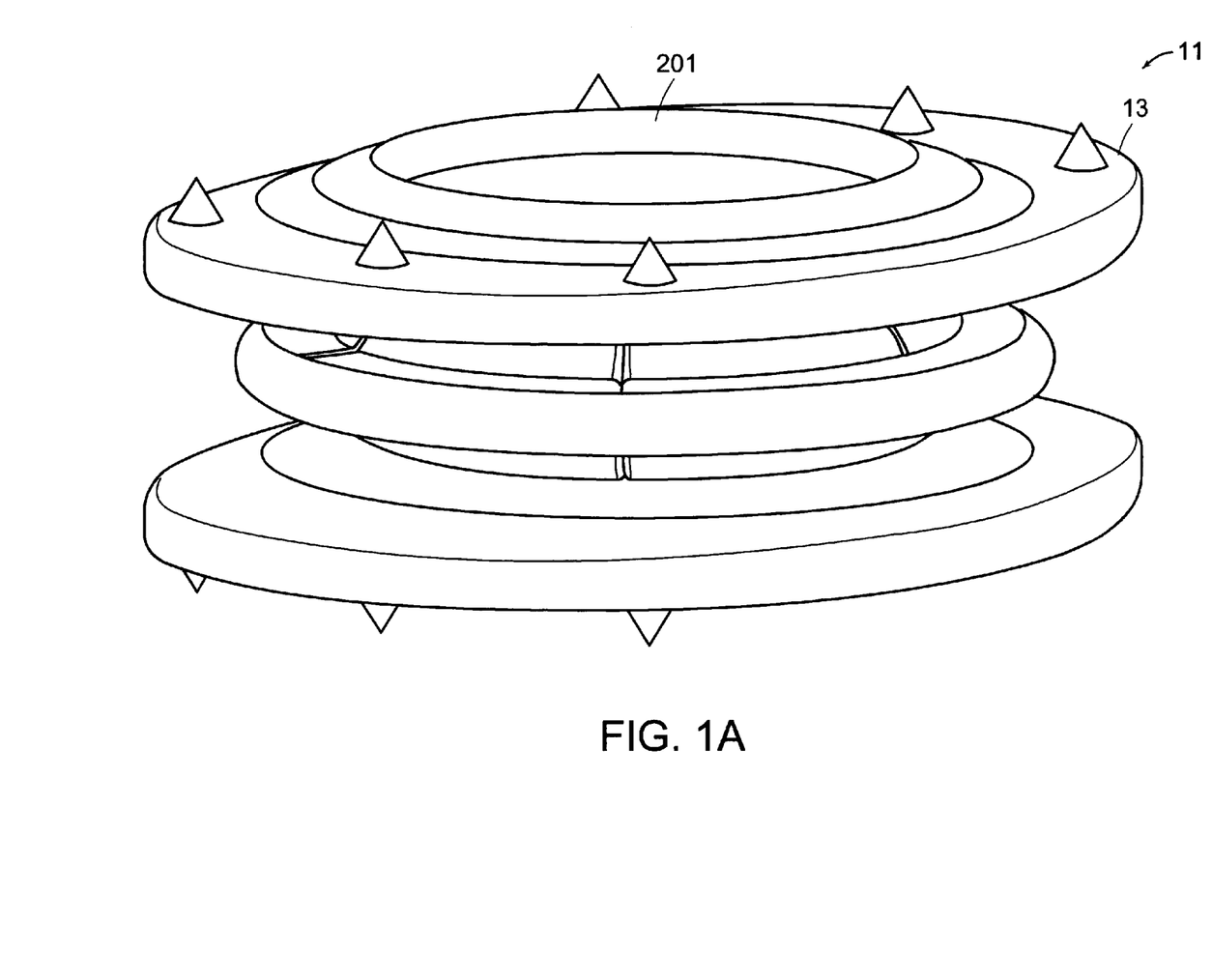
FIG. 1a is a perspective view of a first embodiment of the present invention.
Figure 1B:
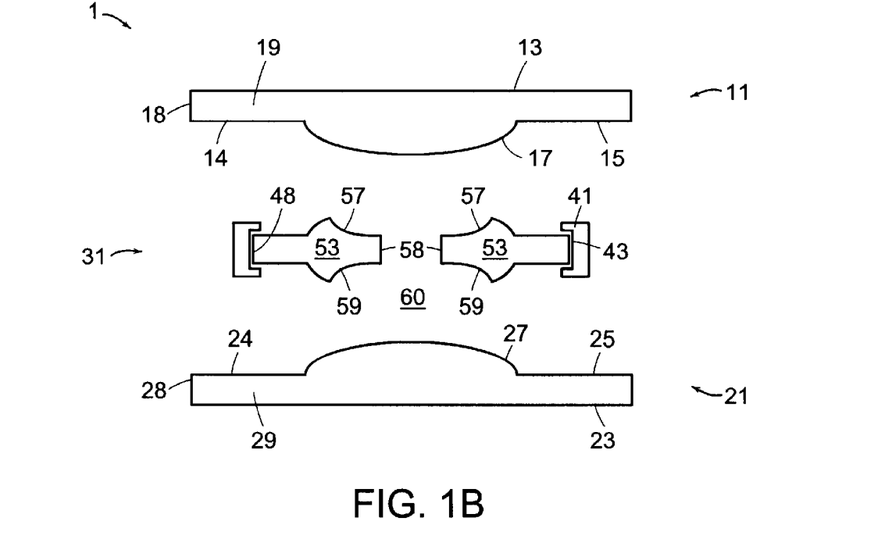
Figure 2:
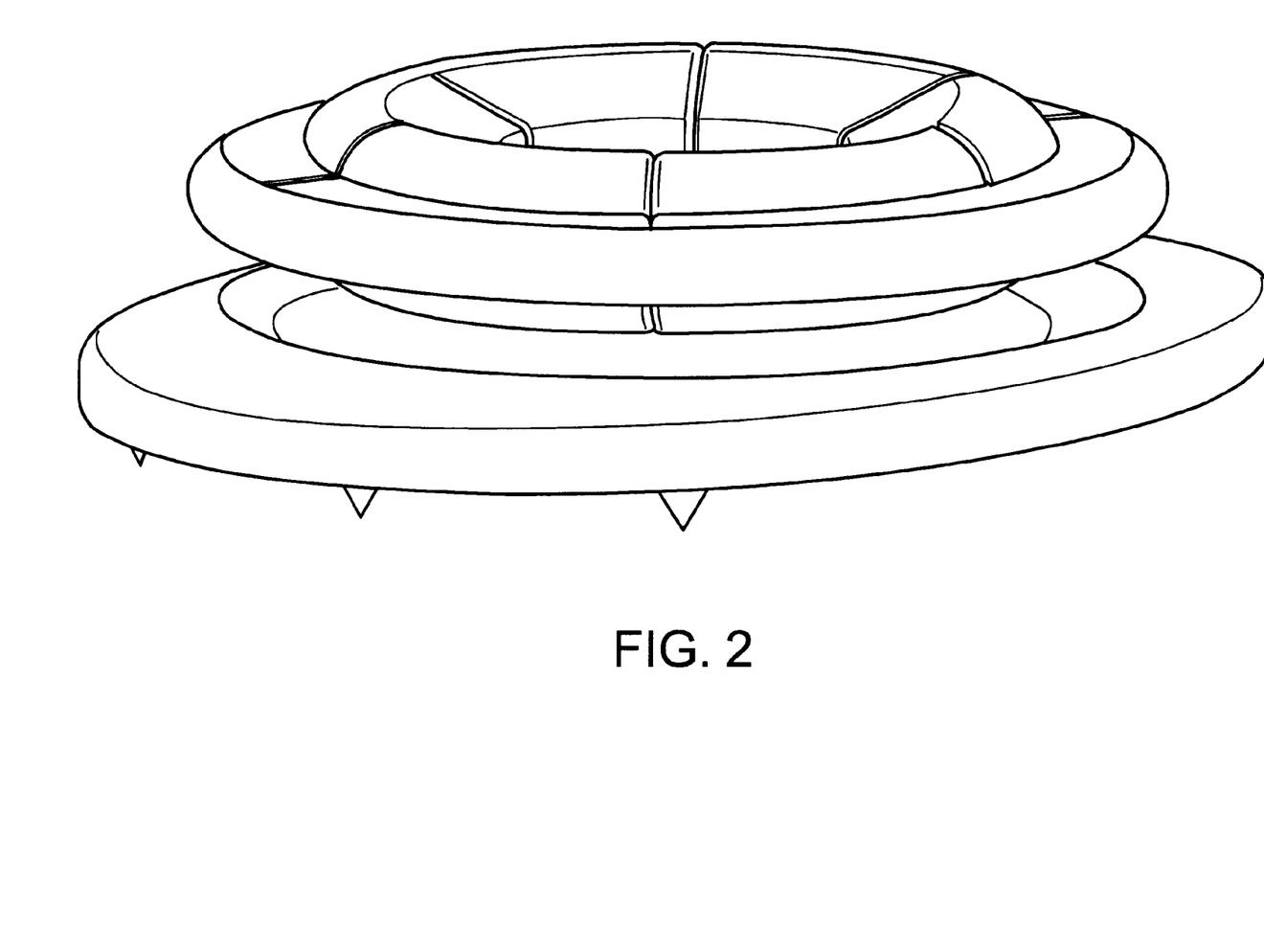
FIG. 2 is a perspective view of the embodiment of FIG. 1, wherein the superior prosthetic endplate has been removed.

Now referring to FIGS. 1a–1b, there is provided a motion disc 1 comprising:
a) a first prosthetic vertebral endplate 11 comprising:
  i) an outer surface 13 adapted to mate with a first vertebral body,
  ii) an inner surface 15 having a first articulation surface 17,
  iii) a body portion 19 connecting the inner and outer surfaces,
b) a second prosthetic vertebral endplate 21 comprising:
  i) an outer surface 23 adapted to mate with a second vertebral body, and
  ii) an inner surface 25 comprising a first articulation surface 27, and
  iii) a body portion 29 connecting the inner and outer surfaces, and
c) a laterally expandable core member 31 comprising:
  i) an annulus 41 having an inner diameter 43, and
  ii) an inner articulation member 51 comprising a plurality of partial articulation components 53, each partial articulation component comprising:
    an outer radius 48 adapted to seat upon the inner diameter of the expandable annulus,
    a first partial articulation surface 57 adapted for articulation with the first articulation surface of the first endplate,
    a second partial articulation surface 59 adapted for articulation with the first articulation surface of the second endplate, wherein the core member is oriented therein to produce a first articulation interface between the first articulation surface of the first endplate and the first articulation surface of the core member, and a second articulation interface between the first articulation surface of the second endplate and the second articulation surface of the core member.

Still referring to FIGS. 1a and 1b, the core member 31 comprises a plurality of partial articulation components, each articulation component 53 having a i) superior partial articulating surface 57 that is designed to articulate with the bottom articulating surface of the superior endplate, and ii) an inferior partial articulating surface 59 that is designed to articulate with the upper articulating surface of the inferior endplate. In use, the plurality of partial articulating components are oriented so that, together, they describe a complete articulation surface.

Preferably, superior articulating surface 57 is further designed to conform to the bottom articulating surface 17 of the superior endplate. Also preferably, inferior articulating surface 59 is designed to conform with a corresponding articulating surface of the inferior endplate.

The partial articulating surfaces of the core member can be combined to produce a complete articulating surface having any shape designed for pivotal articulation, including hemispherical, hemicylindrical, hemi-ellipsoidal, and oblong. However, in preferred embodiments, the complete articulating surface forms at least a portion of a hemi-sphere.

In the preferred embodiments, the complete articulation surfaces of the core are each concave. However, the complete articulation surfaces can also be convex, if desired, to mate with a corresponding substantially concave articulation surface disposed upon an endplate.

In some embodiments, the laterally expandable core member expands laterally when the disc is subjected to axial load of about 750 pounds force (3.4 kN) to reduce the height of the device between 0.5 and 1.5 mm, more preferably 0.8 mm–1.2 mm.

In some embodiments, the core member comprises:
i) an annulus having an inner diameter, and
ii) an inner articulation member comprising a plurality of partial articulation components, each articulation component comprising:
an outer radius adapted to seat upon the inner diameter of the expandable annulus,
a first partial articulation surface adapted for articulation with the first articulation surface of the first endplate,
a second partial articulation surface adapted for articulation with the first articulation surface of the second endplate, Providing a plurality of partial articulation components is advantageous because each partial articulating surface can be adapted to independently slide radially away from the center of the corresponding articulating surface of the adjacent endplate in response to an axial load. This radial sliding feature allows that adjacent prosthetic endplates closer to one another, thereby mimicking the natural shock-absorbing feature of the natural disc.

Figure 3:
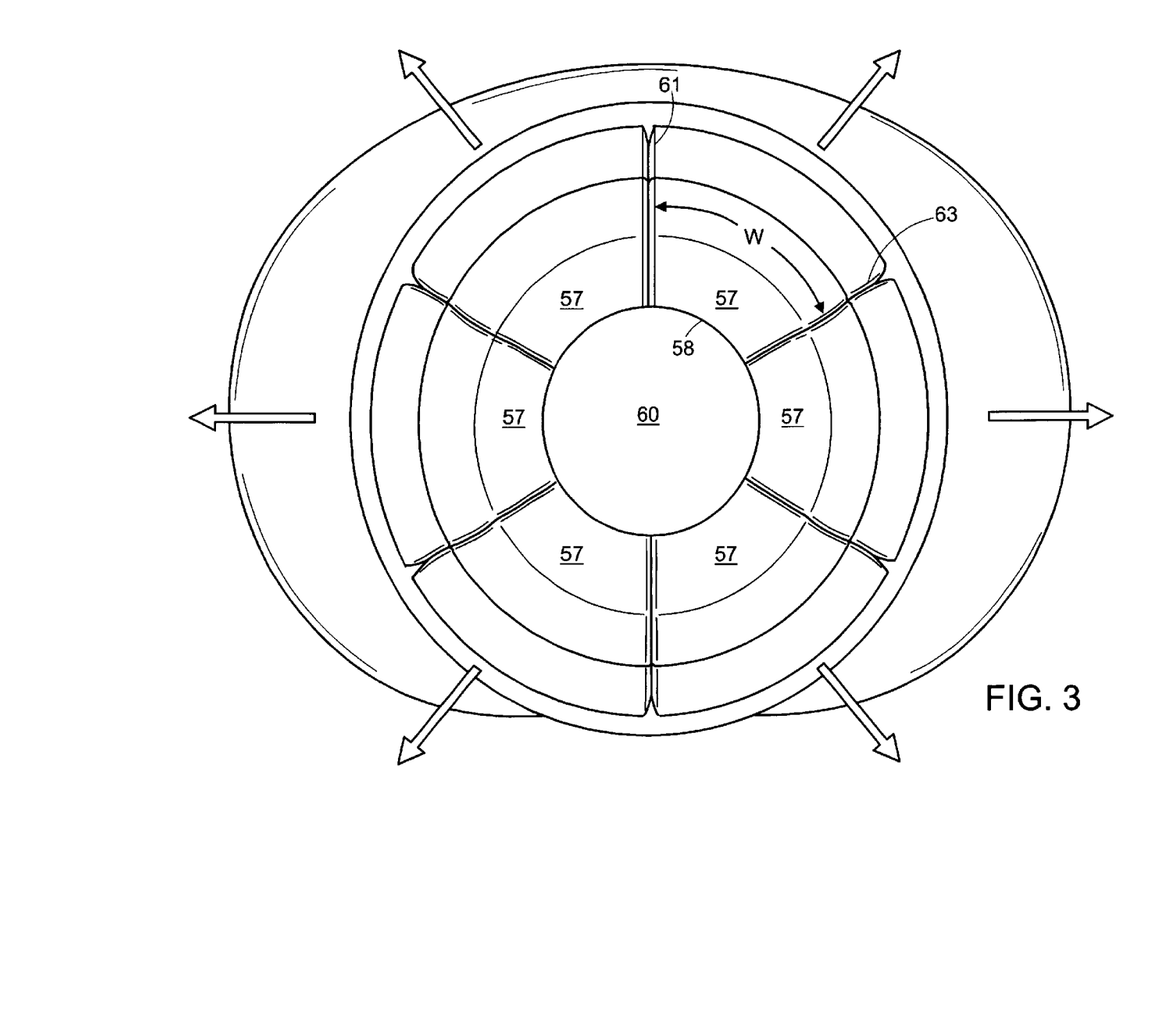
FIG. 3 is a top view of FIG. 2

In some embodiments, as in FIG. 3, the complete articulation member comprises at least three partial articulation components. For example, FIG. 3 discloses six partial articulating components. The provision of at least three partial articulation components allows for a more circumferentially even radial movement of the pieces of the core member, and thereby more closely mimicking the shock absorbing feature of the natural disc.

In some embodiments, as in FIG. 1b, the inner radius 43 of the expandable annulus 41 forms a groove and the outer radius 48 of each partial articulation component has a lip adapted to seat in the groove, thereby providing for stable motion between the annulus and partial articulation components without detachment. However, in other embodiments, the inner radius of the expandable annulus may be convex and seat upon a concave outer radius of each partial articulation component.

In some embodiments, as in FIG. 3, each partial articulation component comprises an inner radius 58. The provision of an inner radius in each partial articulation component produces an even larger central hole 60 in the middle of the core member during axial loading, thereby allowing the prosthetic endplates to move even closer to one another (through the hole) and mimic the natural response of the disc.

In some embodiments, as in FIG. 3, each partial articulation component has first 61 and second 63 side surfaces defining a width W therebetween, wherein the width of each articulation component decreases inwardly. The "decreasing width" feature allows each of the plurality of partial articulation components to seat upon the inner portion of the annulus without interference from the adjacent partial articulating components.

In some embodiments, as in FIG. 3, the side surfaces of each partial articulation component define a frustoconcial cross-section. This design allows the core to accommodate at least three partial articulation components, thereby providing more even radial movement.

In some embodiments, as in FIG. 3, the side surfaces of adjacent partial articulation components are closely adjacent each other. This feature provides for efficient use of the space within the core component, thereby providing a more even response.

Figure 4:
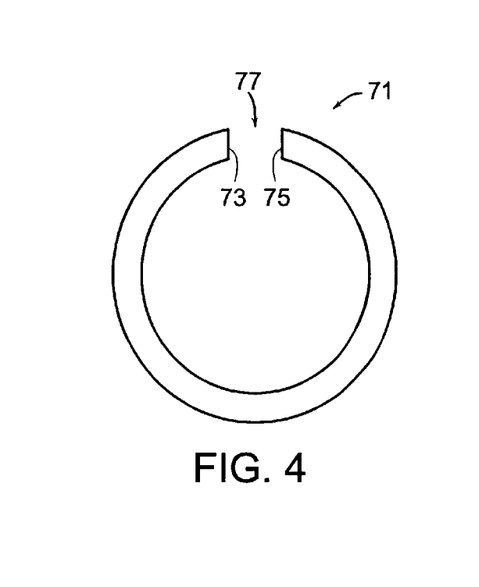
FIG. 4 is a top view of split ring embodiment of the annulus of the present invention.

Now referring to FIG. 4, in some embodiments, the annulus is a split ring 71. The split ring has a first end 73 and a second end 75. In some embodiments, the ring extends less than one full revolution of the circle described by the radius of the split ring, so that a break 77 can be seen from a top view. Preferably, the split ring circumscribes between 95% and 99.9% of that circle, and the break constitutes the remaining 0.1 to 5% of the circle. The split ring design is advantageous because the break allows the annulus to expand in response to outward radial movement of the partial articulating components. When the split ring is made of metal, composite or elastomer, in some embodiments, the split ring design allows the laterally expandable core member to expand laterally when the disc is subjected to axial load of about 750 pounds force (3.4 kN) to reduce the height of the device between 1.0 and 2.0 mm.

Figures 5A, 5B:
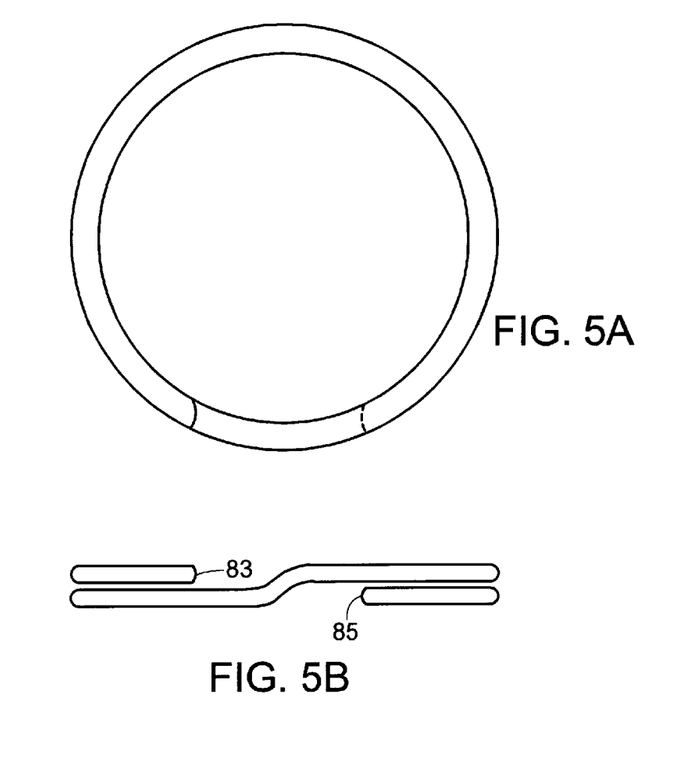
FIGS. 5a and 5b are respective top and side views of a key ring embodiment of the annulus of the present invention.

Now referring to FIGS. 5a and 5b, in other embodiments, the annulus has a key ring shape, and comprises a first end 83 and a second end 85, wherein the ring extends more than one full revolution so that the first and second ends can overlap when viewed from above. Preferably, as in FIGS. 5a and 5b, the key ring annulus extends between 1.5 and 2 revolutions. The key ring embodiment is advantageous because the expansion of the annulus is distributed more evenly to the partial articulating components, and so resists the free radial movement of the partial articulating components somewhat more than the split-ring embodiment of FIG. 4. When the key ring design is made of metal, composite or elastomer, in some embodiments, the key ring design allows the laterally expandable core member to expand laterally when the disc is subjected to axial load of about 750 pounds force (3.4 kN) to reduce the height of the device between 0.5 and 1.5 mm, and so is more closely mimics the natural response (~1 mm) than the split ring embodiment of FIG. 1.

In some embodiments, the annulus is a continuous ring. The continuous ring shape is more desirable than the split ring shapes because the resistance of the annulus expansion is evenly distributed around the articulating components.

Figure 6:
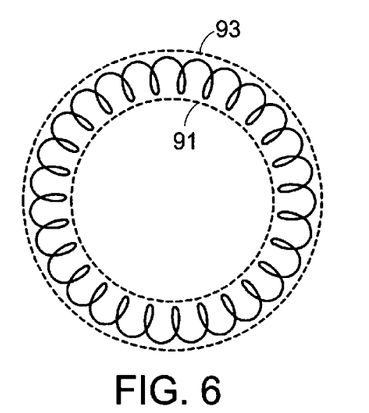
FIG. 6 is a top view of a coil embodiment of the annulus of the present invention.

Now referring to FIG. 6, in other embodiments, the continuous annulus has a coil shape, and defines an inner surface 91 and an outer surface 93 (depicted as dotted lines). The continuous coil shape is advantageous because of its ease of amnufacturing. When the continuous coil shape is made of metal, in some embodiments, the design allows the laterally expandable core member to expand laterally when the disc is subjected to axial load of about 750 pounds force (3.4 kN) to reduce the height of the device between 1.0 and 2.0 mm, and so is more mimics the natural response (~1 mm) about as well as the split ring embodiment of FIG. 4.

Figure 7:
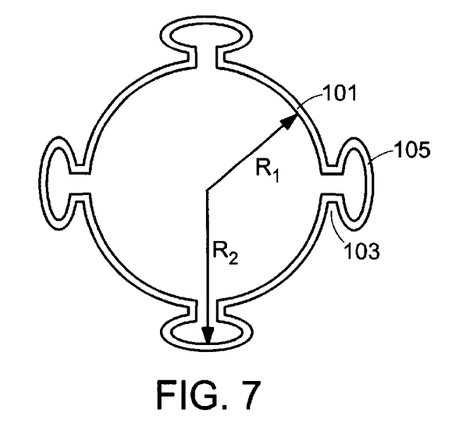
FIG. 7 is a top view of another embodiment of an annulus of the present invention.

Now referring to FIG. 7, in other embodiments, the continuous annulus has a first portion 101 having a smaller radius $R_1$ and a second portion 101 having a necked portion 103 extending into a cavity portion 105 defining a larger radius $R_2$. In use, when the disc bears a significant axial load, the necked portion acts as a spring and advantageously to accommodate the load. When this embodiment is made of metal, in some embodiments, the laterally expandable core member may expand laterally when the disc is subjected to axial load of about 750 pounds force (3.4 kN) to reduce the height of the device between 0.5 and 1.5 mm, and so is more closely mimics the natural response (~1 mm) than the split ring embodiment of FIG. 4.

Figure 8:
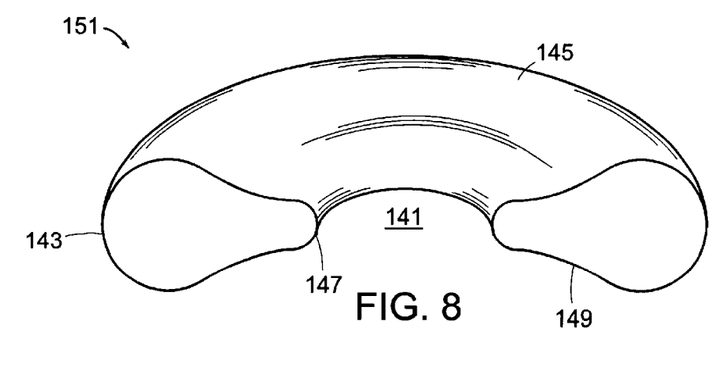
FIG. 8 is a cross-sectional view of an embodiment of the present invention wherein the core member is integral and has a central core.

Now referring to FIG. 8, in some embodiments, the core component 151 is integral and comprises:
i) an outer radius 143 adapted to seat upon the inner diameter of the expandable annulus,
ii) an inner radius 147 defining a central through hole 141,
iii) a first articulation surface 145 adapted for articulation with the first articulation surface of the first endplate,
iv) a second articulation surface 149 adapted for articulation with the first articulation surface of the second endplate.

When this embodiment is made of plastic, such as polyolefins or PEEK, in some embodiments, the laterally expandable core member may expand laterally when the disc is subjected to axial load of about 750 pounds force (3.4 kN) to reduce the height of the device between 0.5 and 0.7 mm, and so somewhat mimics the natural response (~1 mm) of the intervertebral disc.

For the purposes of the present invention, "prosthetic vertebral endplate" broadly describes a component designed to substantially fit within an interverterbal space and mate with an opposing surface of one of the adjacent vertebral bodies. The "prosthetic vertebral endplate" includes all geometric configurations, including but not limited to substantially thin and substantially blocky configurations. Types of mating include, but are not limited to, penetrating the adjacent vertebral body, simply contacting the adjacent vertebral body, and providing fixation through a third component such as a fastener (such as a screw) that is received within or connected to the prosthetic vertebral endplate. Such fixation may occur upon a non-opposing surface of the adjacent vertebral body (such as the anterior wall of the vertebral body). The adjacent vertebral body may be prepared or unprepared so that the contacting surface thereof may include the cortical end endplate portion of the vertebral body or the internal cancellous portion of the vertebral body.

Now referring to FIG. 1b, in one embodiment, inferior endplate 21 has an inferior surface 23 designed to mate with a natural vertebral endplate, a superior surface 25 designed to mate with the core member, and a body portion 29 therebetween. The periphery of the inferior endplate comprises a wall 28.

Preferably, the inferior (outer) surface 23 of this endplate is either flat, curved or domed to match the natural vertebral endplate. Alternatively, the geometry of the inferior surface can be designed so that it will match the shape of the patient's vertebral endplate after the vertebral endplate has been modified by an endplate-shaping instrument. In addition, the inferior surface of this endplate can further comprise features to promote and secure initial fixation and bony ingrowth including, but not limited to, spikes, keels, teeth, projections (such as dovetails), recesses (such as grooves) and porous coatings.

Superior (inner) surface 25 comprises a peripheral portion 24 and a highly polished substantially convex articulation surface 27 designed to mate with a corresponding substantially concave partial articulation surfaces 59 disposed upon the core member. Preferably, substantially convex articulation surface 27 is further designed to conform to the corresponding partial concave articulation surfaces 59. In the preferred embodiment the articulation surface 27 is convex. Preferably, the substantially curved articulation surface 27 has been polished to a surface roughness Ra of no more than 10 nm.

Now referring to FIG. 1b, in one embodiment, superior endplate 11 has a superior surface 13 designed to mate with a natural vertebral endplate, an inferior surface 15 designed to mate with the core member, and a body portion 19 therebetween. The periphery of the superior endplate comprises a wall 18.

Preferably, the superior (outer) surface 13 of this endplate is either flat, curved or domed to match the natural vertebral endplate. Alternatively, the geometry of the inferior surface can be designed so that it will match the shape of the patient's vertebral endplate after the vertebral endplate has been modified by an endplate-shaping instrument. In addition, the superior surface of this endplate can further comprise features to promote and secure initial fixation and bony ingrowth including, but not limited to, spikes, keels, teeth, projections (such as dovetails), recesses (such as grooves) and porous coatings.

Inferior (inner) surface 15 comprises a peripheral portion 14 and a highly polished substantially convex articulation surface 17 designed to mate with a corresponding substantially concave articulation surface (not shown) disposed upon the core member. Preferably, substantially convex articulation surface 17 is further designed to conform to the corresponding partial concave articulation surfaces 57. Preferably, substantially convex articulation surface 17 is further designed to conform to the corresponding concave articulation surface 57. Preferably, the substantially curved articulation surface 17 has been polished to a surface roughness Ra of no more than 10 nm.

In preferred embodiments, each of the inferior endplate, superior endplate and core member is manufactured from a material that possesses the strength and high wear resistance desired for use as a motion disc component.

These components of the present invention may be made from any non-resorbable material appropriate for human surgical implantation, including but not limited to, surgically appropriate metals, and non-metallic materials, such as carbon fiber composites, polymers and ceramics.

If a metal is chosen as the material of construction for a component, then the metal is preferably selected from the group consisting of titanium, titanium alloys (such as Ti-6Al-4V), chrome alloys (such as CrCo or Cr—Co—Mo) and stainless steel.

If a polymer is chosen as a material of construction for a component, then the polymer is preferably selected from the group consisting of polyesters, (particularly aromatic esters such as polyalkylene terephthalates, polyamides; polyalkenes; poly(vinyl fluoride); PTFE; polyarylethyl ketone PAEK; and mixtures thereof.

If a ceramic is chosen as the material of construction for a component, then the ceramic is preferably selected from the group consisting of alumina, zirconia and mixtures thereof. It is preferred to select an alumina-zirconia ceramic, such as BIOLOX delta™, available from CeramTec of Plochingen, Germany. Depending on the material chosen, a smooth surface coating may be provided thereon to improve performance and reduce particulate wear debris.

In some preferred embodiments, the articulation components of the core member consist essentially of a ceramic, preferably a sintered polycrystalline ceramic. Preferably, the sintered polycrystalline ceramic comprises at least 50 wt % of a material selected from the group consisting of synthetic diamond, alumina, zirconia, and alumina-zirconia mixtures. In some alumina-zirconia mixture embodiments, the ceramic comprises 10–30 wt % alumina.

In some alumina-zirconia mixture embodiments, the ceramic comprises 70–90 wt % alumina. In some embodiments, the ceramic comprises alumina having a median grain size of no more than 5 micron, preferably less than 3 microns, more preferably less than 2 microns, more preferably less than one micron. In some embodiments, the ceramic comprises tetragonal zirconia having a median grain size of no more 2 microns, more preferably less than one micron. In some embodiments, the ceramic comprises alumina made from a seeded gel process.

In some embodiments, the articulation components of the core member are polyethylene.

In some preferred embodiments, the first endplate consists essentially of a metallic material, preferably a titanium alloy or a chrome-cobalt alloy. In some preferred embodiments, the second endplate consists essentially of the same metallic material as the first plate.

In some embodiments, the articulation surfaces of the endplates may be coated with a wear-resistant coating, such as diamond film, in order to reduce wear.

In some embodiments, the endplates are made of a titanium alloy, preferably BioDur® CCM Plus® Alloy available from Carpenter Specialty Alloys, Carpenter Technology Corporation of Wyomissing, Pa.; and the core member is made of polyethylene, preferably Marathon™, available from DePuy Orthopaedics of Warsaw, Ind. In some embodiments, the endplate articulation surfaces are coated with a sintered bead coating, preferably Poracoat™, available from DePuy Orthopaedics of Warsaw, Ind.

In some embodiments, the endplates are made from a composite comprising carbon fiber. Composites comprising carbon fiber are advantageous in that they typically have a strength and stiffness that is superior to neat polymer materials such as a polyarylethyl ketone PAEK.

Preferably, the composite comprising carbon fiber further comprises a polymer. Preferably, the polymer is a polyarylethyl ketone PAEK. More preferably, the PAEK is selected from the group consisting of polyetherether ketone PEEK, polyether ketone ketone PEKK and polyether ketone PEK. In preferred embodiments, the PAEK is PEEK.

In some embodiments, the carbon fiber comprises between 1 vol % and 60 vol % (more preferably, between 10 vol % and 50 vol %) of the composite. In some embodiments, the polymer and carbon fibers are homogeneously mixed. In others, the material is a laminate. In some embodiments, the carbon fiber is present as chopped state. Preferably, the chopped carbon fibers have a median length of between 1 mm and 12 mm, more preferably between 4.5 mm and 7.5 mm. In some embodiments, the carbon fiber is present as continuous strands.

In especially preferred embodiments, the composite comprises:
   a) 40–99% (more preferably, 60–80 vol %) polyarylethyl ketone PAEK, and
   b) 1–60% (more preferably, 20–40 vol %) carbon fiber,
wherein the polyarylethyl ketone PAEK is selected from the group consisting of polyetherether ketone PEEK, polyether ketone ketone PEKK and polyether ketone PEK.

In some embodiments, the composite consists essentially of PAEK and carbon fiber. More preferably, the composite comprises 60–80 wt % PAEK and 20–40 wt % carbon fiber. Still more preferably the composite comprises 65–75 wt % PAEK and 25–35 wt % carbon fiber.

Now referring to FIG. 1a, in some embodiments, the outer surfaces of the endplates may have a recess 201 therein. In some embodiments, the recess may be filled with a porous material (not shown), including osteobiologic materials, adapted for bone growth.

Although the present invention has been described with reference to its preferred embodiments, those skillful in the art will recognize changes that may be made in form and structure which do not depart from the spirit of the invention.

I claim:

1. An intervertebral motion disc comprising:
   a) a first prosthetic vertebral endplate comprising:
      i) an outer surface adapted to mate with a first vertebral body,
      ii) an inner surface having a first articulation surface,
      iii) a body portion connecting the inner and outer surfaces,
   b) a second prosthetic vertebral endplate comprising:
      i) an outer surface adapted to mate with a second vertebral body, and
      ii) an inner surface comprising a first articulation surface, and
      iii) a body portion connecting the inner and outer surfaces, and
   c) a laterally expandable core member comprising:
      a first articulation surface adapted for articulation with the first articulation surface of the first endplate,
      a second articulation surface adapted for articulation with the first articulation surface of the second endplate,
   wherein the core member is oriented therein to produce a first articulation interface between the first articulation surface of the first endplate and the first articulation surface of the core member, and a second articulation interface between the first articulation surface of the second endplate and the second articulation surface of the core member, and a height H between the outer surfaces of the prosthetic endplates, and
   wherein the laterally expandable core member expands laterally when the disc is subjected to axial load of about 750 pounds force (3.4 kN) to reduce the height of the device between 0.5 and 2.0 mm; and
   wherein the core member comprises:
      i) an annulus having an inner diameter, and
      ii) an inner articulation member comprising a plurality of articulation components, each articulation component comprising:
         an outer radius adapted to sear upon the inner diameter of the expandable annulus,
         a first articulation surface adapted for articulation with the first articulation surface of the first endplate,
         a second articulation surface adapted for articulation with the first articulation surface of the second endplate.

2. The disc of claim 1 wherein the laterally expandable core member expands laterally when the disc is subjected to axial load of about 750 pounds force (3.4 kN) to reduce the height of the device between 0.5 and 1.5 mm.

3. The disc of claim 1 wherein the laterally expandable core member expands laterally when the disc is subjected to axial load of about 750 pounds force (3.4 kN) to reduce the height of the device between 0.8 and 1.2 mm.

4. The disc of claim 1 wherein the annulus is expandable.

5. The disc of claim 4 wherein the annulus is continuous.

6. The disc of claim 5 wherein the continuous annulus is a coil.

7. The disc of claim 5 wherein the continuous annulus has a first portion having a smaller outer radius and a second portion having a larger outer radius.

8. The disc of claim 4 wherein the annulus has a first end and a second end.

9. The disc of claim 8 wherein the annulus has a key ring shape.

10. The disc of claim 4 wherein the annulus is a split ring.

11. The disc of claim 1 wherein the inner articulation member comprises at least three articulation components.

12. The disc of claim 1 wherein the annulus has a groove and the outer radius of each articulation component has a lip adapted to seat in the groove.

13. The disc of claim 1 wherein each articulation component comprises an inner radius.

14. The disc of claim 1 wherein each articulation component has first and second side surfaces defining a width therebetween, wherein the width of each articulation component decreases inwardly.

15. The disc of claim 1 wherein the side surfaces of each articulation component form a frustoconcial cross-section.

16. The disc of claim 1 wherein the side surfaces of adjacent articulation components contact each other.

17. The disc of claim 1 wherein the core member is an integral body having a central hole.

18. An intervertebral motion disc comprising:
   a) a first prosthetic vertebral endplate comprising:
      i) an outer surface adapted to mate with a first vertebral body,
      ii) an inner surface having a first articulation surface,
      iii) a body portion connecting the inner and outer surfaces,
   b) a second prosthetic vertebral endplate comprising:
      i) an outer surface adapted to mate with a second vertebral body, and
      ii) an inner surface comprising a first articulation surface, and
      iii) a body portion connecting the inner and outer surfaces, and
   c) a laterally expandable core member comprising:
      i) an annulus having an inner diameter, and
      ii) an inner articulation member comprising a plurality of articulation components, each articulation component comprising:
         an outer radius adapted to seat upon the inner diameter of the expandable annulus,
         a first articulation surface adapted for articulation with the first articulation surface of the first endplate,
         a second articulation surface adapted for articulation with the first articulation surface of the second endplate,
   wherein the core member is oriented therein to produce a first articulation interface between the first articulation surface of the first endplate and the first articulation surface of the core member, and a second articulation interface between the first articulation surface of the second endplate and the second articulation surface of the core member.

* * * * *